Figure 1:
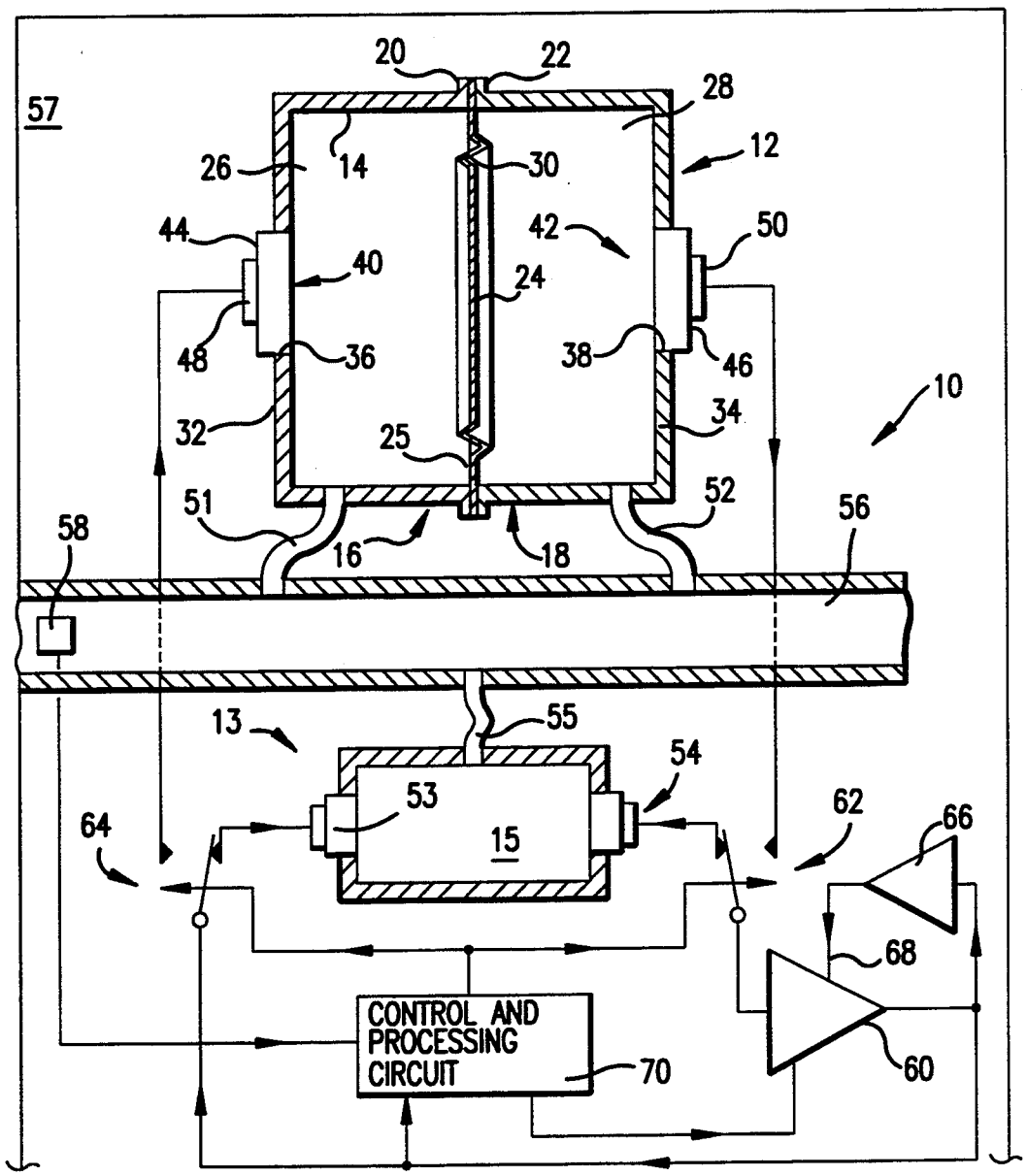

United States Patent [19]

Dames

[11] Patent Number: 5,386,714
[45] Date of Patent: Feb. 7, 1995

[54] RESONANT CAVITY GAS DENSITY SENSOR

[75] Inventor: Andrew N. Dames, Milton, England

[73] Assignee: Schlumberger Industries Limited, London, United Kingdom

[21] Appl. No.: 75,576

[22] PCT Filed: Dec. 5, 1991

[86] PCT No.: PCT/GB91/02156
§ 371 Date: Jul. 22, 1993
§ 102(e) Date: Jul. 22, 1993

[87] PCT Pub. No.: WO92/11532
PCT Pub. Date: Jul. 9, 1992

[30] Foreign Application Priority Data
Dec. 22, 1990 [GB] United Kingdom ............... 9027989

[51] Int. Cl.[6] ............... G01N 29/02; G01N 4/00; G01L 9/08
[52] U.S. Cl. ............... 73/24.05; 73/30.04; 73/32 A
[58] Field of Search ............... 73/24.05, 32 A, 30.04

[56] References Cited
U.S. PATENT DOCUMENTS

| | | | |
|---|---|---|---|
| 3,295,360 | 1/1967 | Dimeff | 73/24.05 |
| 4,262,523 | 4/1981 | Stansfeld | 73/24.05 |
| 4,872,335 | 10/1989 | Tsuruoka et al. | 73/24.05 X |
| 4,961,345 | 10/1990 | Tsuruoka et al. | 73/32 A |
| 5,159,843 | 11/1992 | Shakkottai et al. | 73/24.05 |

Primary Examiner—Hezron E. Williams
Assistant Examiner—Joseph W. Roskos
Attorney, Agent, or Firm—Sanford J. Asman

[57] ABSTRACT

A density sensor comprises a cavity arranged to receive the gas whose density is to be sensed. The cavity is divided into two chambers by a flexibly mounted diaphragm. A piezoelectric excitation device at one end of the cavity is used to excite the gas in the cavity into resonant vibration in a mode having an anti-node at the diaphragm, which causes the diaphragm to vibrate with the gas. Another piezoelectric device senses the vibration, whose frequency is a function of the known mass of the diaphragm and the density and speed of sound in the gas. This last parameter can be sensed by exciting the gas in the cavity into resonant vibration in a second mode having a node at the diaphragm, so that the diaphragm does not take part in the vibration. Alternatively, it can be sensed by providing a second cavity, also arranged to receive the gas but not having a diaphragm, and resonantly vibrating the gas in the second cavity.

28 Claims, 2 Drawing Sheets

RESONANT CAVITY GAS DENSITY SENSOR

This application is a 371 of PCT/GB91/02156 filed on Dec. 5, 1991.

This invention relates to sensors, and is more particularly but not exclusively concerned with gas density sensors suitable for use in domestic gas metering.

There have been several proposals recently for domestic gas meters incorporating solid state or other electrically operated devices which sense volumetric flow rate. However, it is now increasingly being thought desirable that domestic gas metering should be based upon a mass flow rate measurement rather than a volumetric flow rate measurement. This can be achieved by measuring the density of the gas as well as its volumetric flow rate, and then combining the two measurements.

There exists a need, therefore, for a sensor which can be used to measure gas density in a domestic gas metering context. However, use in this context requires that the sensor should be capable of being inexpensively mass produced, and should use as little or less power for its operation as the associated solid state or other volumetric flow rate sensing device. It is an object of the present invention to provide such a sensor.

According to one aspect of the present invention, there is provided a sensor for use in determining the density of a gas, the sensor comprising:
a cavity arranged to receive the gas whose density is to be determined;
dividing means dividing the cavity into two distinct chambers, the dividing means being at least partly movable within the cavity;
excitation mean for exciting the gas in the cavity into resonant vibration in a mode in which the dividing means vibrates with the gas;
pick-up means for sensing the frequency of said resonant vibration; and
means for producing a signal representative of the velocity of sound in the gas;
whereby the density of the gas may be determined from said frequency and said signal representative of the velocity of sound in the gas.

The excitation means may be additionally arranged to excite the gas in the cavity into resonant vibration in a second mode in which the dividing means does not significantly take part in the vibration of the gas, and the pick-up means may be arranged to sense the frequency of said second mode of resonant vibration, the frequency of said second mode of resonant vibration serving as said signal representative of the velocity of sound in the gas.

Alternatively, the signal producing means may comprise a second cavity arranged to receive the gas whose density is to be determined, second excitation means for exciting the gas in the second cavity into resonant vibration, and second pick-up means for sensing the frequency of resonant vibration of the gas in the second cavity, the frequency of resonant vibration of the gas in the second cavity serving as said signal representative of the velocity of sound in the gas.

According to a second aspect of the present invention, there is provided a sensor for use in determining the density of a gas, the sensor comprising:
a cavity arranged to receive the gas whose density is to be determined;
a diaphragm dividing the cavity into two distinct chambers;
excitation means for exciting the gas in the cavity into resonant vibration in a first mode in which the diaphragm vibrates with the gas, and in a second mode in which the diaphragm does not significantly take part in the vibration of the gas; and
pick-up means for sensing the respective frequencies of the first and second modes of vibration;
whereby the density of the gas may be determined from said frequencies.

In a preferred embodiment of this second aspect of the invention, the position of the diaphragm within the cavity and the modes of vibration of the gas are selected such that the first mode has an antinode (or region of maximum gas displacement) at the diaphragm, and the second mode has a node (or region of minimum gas displacement) at the diaphragm. Thus the diaphragm is preferably positioned substantially midway between the opposite ends of the cavity, whereby the two chambers are of substantially equal length, and the first and second modes are preferably modes 1 and 2 respectively.

According to a third aspect of the invention, there is provided a sensor for use in determining the density of a gas, the sensor comprising:
first and second cavities each arranged to receive a gas whose density is to be determined;
a diaphragm dividing the first cavity into two distinct chambers;
first excitation means for exciting the gas in the first cavity into resonant vibration in a mode in which the diaphragm vibrates with the gas;
first pick-up means for sensing the frequency of the vibration of the gas in the first cavity;
second excitation means for exciting the gas in the second cavity into resonant vibration; and
second pick-up means for sensing the frequency of the vibration of the gas in the second cavity;
whereby the density of the gas may be determined from said frequencies.

In a preferred embodiment of this third aspect of the invention, the dimensions of the second cavity and/or the mode of vibration of the gas therein are selected such that the respective frequencies of vibration of the gas in the two cavities are similar. Additionally, the position of the diaphragm within the first cavity and the mode of vibration of the gas in the first cavity are again selected such that the mode has an antinode at the diaphragm, in which case the diaphragm is preferably positioned substantially midway between the opposite ends of the first cavity, whereby the two chambers are of substantially equal length, and the mode of vibration of the gas in the first cavity is preferably the first mode.

In embodiments in accordance with all three aspects of the invention, the excitation means and the pick-up means are piezoelectric.

Advantageously, the or each cavity is substantially cylindrical, with its excitation means mounted in one end wall and its pick-up means mounted in the other end wall.

Each chamber may have a respective common inlet and outlet adapted to communicate with a pipe through which the gas whose density is to be determined flows, whereby the gas circulates into each chamber by diffusion. Alternatively, each chamber may have an inlet and an outlet, and the gas whose density is to be determined may be arranged to flow through both chambers in parallel.

Figure 2:
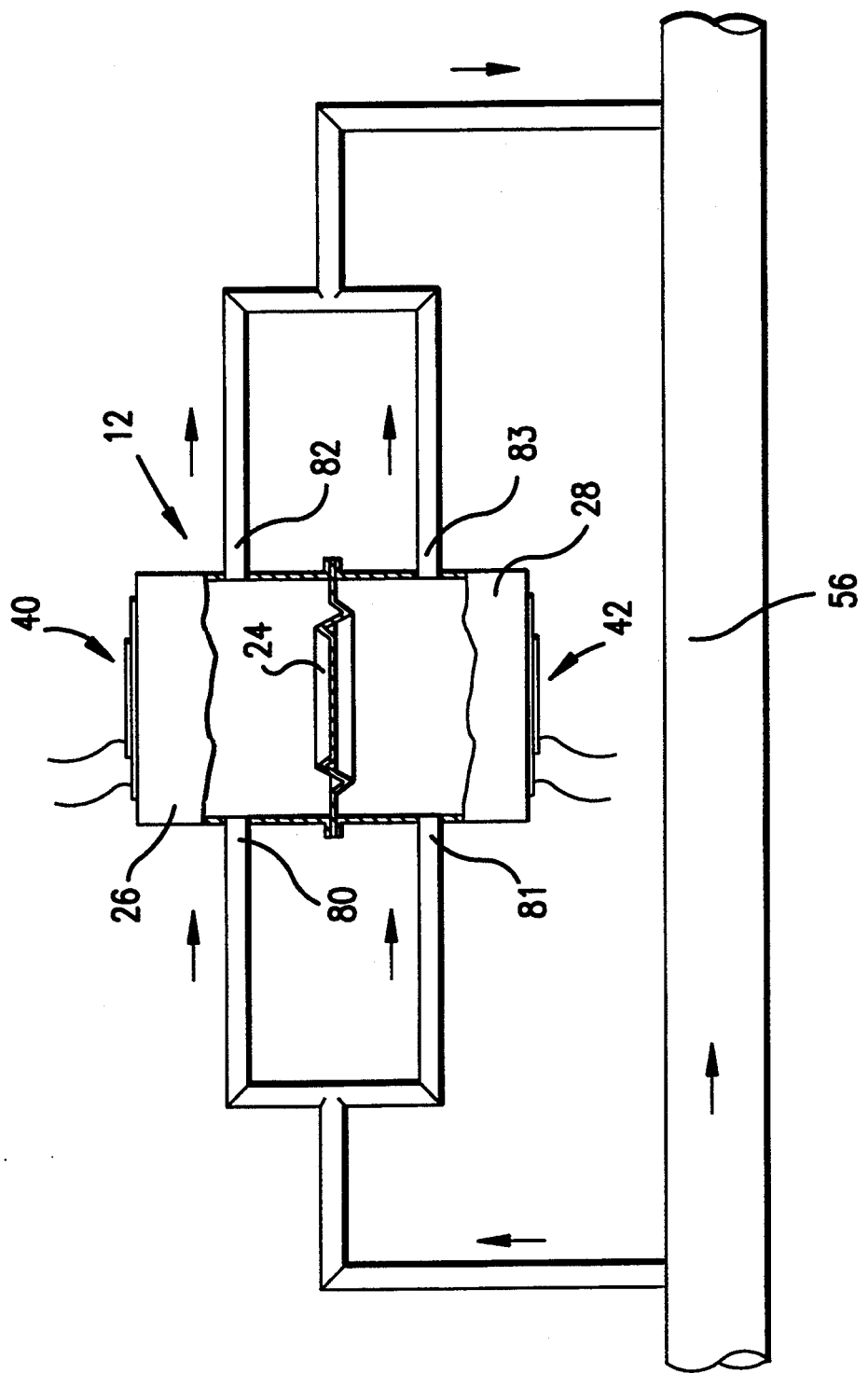

The invention will now be described, by way of example only, with reference to the accompanying drawings, of which:

FIG. 1 is a somewhat schematic representation of a gas density sensor in accordance with the present invention, installed in a domestic gas meter; and FIG. 2 shows an alternative embodiment of part of the sensor of FIG. 1.

The gas density sensor illustrated in FIG. 1 is indicated generally at 10, and comprises first and second generally cylindrical housings 12, 13 defining respective cavities 14, 15. The cavity 14 is about 4 cm in diameter and about 4 cm long, while the cavity 15 is about 1 cm in diameter and about 3 cm long.

The housing 12 is formed in aluminium in two substantially identical halves 16, 18, which are secured together at circumferentially extending flanges 20, 22. A lightweight circular diaphragm 24 has its periphery 25 coaxially and sealingly entrapped between the flanges 20, 22, and thus divides the cavity 14 into two substantially identical chambers 26, 28. The diaphragm 24 is made from a plastics material, and has circumferentially extending corrugations 30 extending all the way around it near its periphery 25.

The housing 12 has end walls 32, 34 having respective openings 36, 38 formed in them. A piezoelectric excitation device 40 is sealingly mounted in the opening 36 so as to face into the chamber 26, while a piezoelectric pick-up device 42 is sealingly mounted in the opening 38 so as to face into the chamber 28. The piezoelectric devices 40 and 42 are essentially similar to each other, each comprising a brass disc (44 or 46) having a wafer of a piezoelectric material (48 or 50) bonded to it: an electrode (not shown) is deposited on the surface of the piezoelectric wafer remote from the brass disc, electrical connections to the wafer being made via this electrode and the brass disc.

The housing 12 is also provided with a first combined inlet and outlet port 51 which communicates with the chamber 26, and a second combined inlet and outlet port 52 which communicates with the chamber 28.

The housing 13 is similar to the housing 12, except for its smaller dimensions and the fact that it does not contain a diaphragm. The smaller dimensions necessitate the use of slightly smaller piezoelectric excitation and pick-up devices, indicated at 53 and 54 respectively, while the absence of a diaphragm means that only a single combined inlet and output port 55 is required.

In use, the ports 51, 52 and 55 are all connected to a duct 56 through which a gas whose density is to be sensed flows, thus enabling the gas to fill the cavities 14, 15 by diffusion. The duct 56 typically forms part of the gas flow path within a domestic gas meter 57, which also contains a solid state volumetric flow rate sensor 58.

To measure the density of the gas in the cavities 14, 15, the gas is excited into resonant vibration by means of the piezoelectric excitation devices 40, 53 respectively. This is done sequentially, by means of a high gain amplifier 60, tuned to a frequency band covering the expected range of resonant frequencies of the first mode of vibration of the gas in the cavities 14, 15, typically x to y kHz.

The input of the amplifier 60 is selectively connectable via a solid state changeover switching circuit 62 either to the piezoelectric pick-up device 42 or to the piezoelectric pick-up device 54, while the output of the amplifier 60 is selectively connectable via another solid state changeover switching circuit 64, operable in unison with the circuit 62, either to the piezoelectric excitation device 40 or to the piezoelectric excitation device 53, to form a positive feedback loop between each pick-up device and the associated excitation device. The amplifier 60 is provided with an automatic gain control (AGC) circuit 66, which is coupled between the output of the amplifier 60 and its gain control input 68, and helps to prevent the amplifier from saturating as resonance is reached.

The switching circuits 62, 64 are controlled by a combined control and processing circuit 70, which also controls the energisation of the amplifier 60 and may typically comprise a microprocessor.

Assuming the switching circuits 62, 64 are initially in the respective states illustrated in the drawing, upon energisation of the amplifier 60, any slight noise signal from the pick-up device 54 in the frequency band of the amplifier is amplified by the amplifier and applied to the excitation device 53. This is sufficient, by virtue of the positive feedback mentioned earlier, to start the gas in the cavity 15 vibrating resonantly in its first mode, that is the mode in which the localised displacement of the gas increases along the length of the cavity from a minimum (or node) adjacent the excitation device 53 to a maximum (or antinode) at the midpoint, and then decreases to a minimum again adjacent the pick-up device 54. Typically, the circuit 70 allows about one second from energisation of the amplifier 60 for the resonant vibration of the gas in the cavity 15 to become properly established, and then counts the frequency $f_1$ of the vibration for a predetermined period, e.g. one second, and stores the result.

The circuit 70 then sets each of the switching circuits 62, 64 to its other state, and energises the amplifier 60 to cause the gas in the cavity 14 to vibrate resonantly, again in its first mode. It will be appreciated that diaphragm 24 is located at the antinode of the vibration, and is therefore moved by the gas. Because of the flexibility provided by its circumferentially extending peripheral corrugations 30, the diaphragm 24 tends to move as a whole, longitudinally of the cavity 14, with the gas (rather as if it were a piston). Again, the circuit allows about a second for the vibration to become properly established, before counting the frequency $f_2$ of the vibration and storing the result.

The two frequency measurements can be regarded as measurements of the velocity of sound in the free gas (in cavity 15) and of the velocity of sound when the gas is mass loaded with the movable diaphragm (in cavity 14). The ratio of these two measurements thus gives the ratio of the mass of the gas to that of the mass loading. Since the mass of the diaphragm is constant, the mass loading is known, and the density of the gas can therefore be determined. It can be shown that the density $\rho$ of the gas is given to a good approximation by $$\rho = A f_2 / f_1 \tan B f_2 / f_1 \tag{1}$$

where A and B are constants which are mainly dependent upon the dimensions of the cavities 14 and 15 and the mass of the diaphragm, and which can be determined by accurate calibration. The analysis leading to equation (1) assumes that the stiffness resisting the vibrations in each cavity is essentially the same and due solely to the gas, which is a reasonable assumption if the diaphragm 24 is sufficiently flexible around its periphery to move as a whole as mentioned above. However, a small correction for diaphragm stiffness can be made if necessary.

Having effected the measurements of the frequencies $f_1$ and $f_2$, the circuit 70 calculates the density $\rho$ of the gas in accordance with equation (1) or an empirically modified version thereof, incorporates a temperature correction based on a temperature measurement from a temperature sensor (not shown), and combines the result with a volumetric flow rate measurement from the sensor 58. The resulting mass flow rate signal is then integrated over time to give an indication of the total mass of gas supplied via the meter 57.

The gas density sensor 10 has a number of significant advantages. It is relatively small and has no precision machined components, and so is relatively easy and cheap to make. Its power consumption is typically about 1 milliwatt, but its use in the meter 57 typically requires it to effect a fresh density measurement only about once an hour, giving an average power consumption of about 1 microwatt. Furthermore, it is relatively insensitive to gas composition and viscosity.

A number of modifications can be made to the described embodiment of the sensor 10. In particular, the use of the two cavities 14 and 15 is not strictly necessary, since the cavity 14 can be used on its own. Thus the two cavities 14, 15 are used to simplify the choice of the piezoelectric devices 40, 42, 53 and 54 and the design of the amplifier 60, since the dimensions of the cavity 15 are chosen to ensure that the frequency $f_1$ is similar to the frequency $f_2$. However, a more complex circuit can be used to excite the gas in the cavity 14 into resonant vibration in two different modes, thus rendering the cavity 15 unnecessary.

The two different modes used are preferably the first mode, as already described, and the second mode. In the second mode, the gas vibrates such that a node is created in the middle of the length of the cavity 14, i.e. at the diaphragm 24, as well as at each end of the cavity. Since the diaphragm 24 is now located at a node rather than at an antinode, it remains substantially unmoved by the vibration of the gas, and therefore does not significantly affect or contribute to the vibration. The measurement in the second mode therefore serves the same purpose as the measurement in the cavity 15. However, the frequency $f'_1$ of the second mode vibration in the cavity 14 is typically six times the frequency $f_2$, and gas density is given by a relationship of the kind m $f_2/f'_1 = \sqrt{\rho g}/\sqrt{\rho g + m}$ where is the effective mass of the diaphragm 12.

As already indicated, the large difference between $f_2$ and $f'_1$ requires a rather more complex maintaining circuit, for example a circuit involving either respective voltage controlled oscillators which can be phase locked to the respective resonant frequencies of the two modes, or a single voltage controlled oscillator with switchable frequency ranges which can be so phase locked.

As already foreshadowed, the frequency measurement in the free gas, i.e. the frequency measurement in the cavity 15 or in the second vibration mode in the cavity 14, can be regarded as a measurement of the velocity of sound in the free gas. This measurement can therefore be replaced, if desired, by an alternative velocity of sound measurement, e.g. a time-of-flight measurement effected with an ultrasonic sound emitter spaced a known distance from a sound receiver in the gas.

Other modifications which can be made to the sensor 10 include replacing the plastics diaphragm 24, which in practice can simply be a plastics speaker diaphragm from a set of good quality headphones, with a metal diaphragm having more carefully controllable stiffness and temperature characteristics. Alternatively, the diaphragm 24 can be replaced by another suitable dividing means positioned at the centre of the cavity 14, provided that this dividing means has a relatively small suspension stiffness, is relatively undamped by its suspension, and is substantially impermeable to the gas: a spring-centralised piston is one possibility.

Additionally, the housings 12, 13 can be moulded in a suitable plastics material, and can be made smaller than the exemplary dimensions quoted hereinbefore.

Finally, although the gas in the chambers 26, 28 and the cavity 15 changes by diffusion in the sensor 10, this change can be flow-assisted by flow resulting from part of the normal pressure drop generated in the meter 57. Thus the chambers 26, 28 in the cavity 14 can be provided with respective inlets 80, 81 and outlets 82, 83 connected to spaced apart points in the duct 56 between which a pressure difference exists, such that the gas flows through both of the chambers 26, 28 in parallel: such an arrangement is shown schematically in FIG. 2. Similarly, the cavity 15 can be provided with both an inlet and an outlet adjacent its opposite ends.

I claim:

1. A sensor for use in determining the density of a gas, the sensor comprising:

a cavity arranged to receive the gas whose density is to be determined; and dividing means dividing the cavity into two distinct chambers, the dividing means being at least partly movable within the cavity;

the sensor being characterised by:

excitation means for exciting the gas in the cavity into resonant vibration in a mode in which the dividing means vibrates with the gas;

pick-up means for sensing the frequency of said resonant vibration; and means for producing a signal representative of the velocity of sound in the gas, whereby the density of the gas may be determined from said frequency and said signal representative of the velocity of sound in the gas.

2. A sensor as claimed in claim 1, wherein the excitation means is additionally arranged to excite the gas in the cavity into resonant vibration in a second mode in which the dividing means does not significantly take part in the vibration of the gas, and the pick-up means is arranged to sense the frequency of said second mode of resonant vibration, the frequency of said second mode of resonant vibration serving as said signal representative of the velocity of sound in the gas.

3. A sensor as claimed in claim 2, wherein the position of the dividing means within the cavity and the modes of vibration of the gas are selected such that the first mode has an antinode at the dividing means, and the second mode has a node at the dividing means.

4. A sensor as claimed in claim 3, wherein the dividing means is positioned substantially midway between the opposite ends of the cavity, whereby the two chambers are of substantially equal length, and the first and second modes are modes 1 and 2 respectively.

5. A sensor as claimed in claim 1, wherein the signal producing means comprises a second cavity arranged to receive the gas whose density is to be determined, second excitation means for exciting the gas in the second cavity into resonant vibration, and second pick-up means for sensing the frequency of resonant vibration of the gas in the second cavity, the frequency of resonant vibration of the gas in the second cavity serving as said signal representative of the velocity of sound in the gas.

6. A sensor as claimed in claim 5, wherein the dimensions of the second cavity and/or the mode of vibration of the gas therein are selected such that the respective frequencies of vibration of the gas in the two cavities are similar.

7. A sensor as claimed in claim 5, wherein the position of the dividing means within the first cavity and the mode of vibration of the gas in the first cavity are selected such that the mode has an antinode at the dividing means.

8. A sensor as claimed in claim 7, wherein the dividing means is positioned substantially midway between the opposite ends of the first cavity, whereby the two chambers are of substantially equal length, and the mode of vibration of the gas in the first cavity is the first mode.

9. A sensor as claimed in claim 1, wherein the dividing means comprises a diaphragm.

10. A sensor as claim in claim 1, wherein the excitation means and the pick-up means are piezoelectric.

11. A sensor as claimed in claim 1, wherein the or each cavity is substantially cylindrical, with its excitation means mounted in one end wall and its pick-up means mounted in the other end wall.

12. A sensor as claimed in claim 1, wherein each chamber has a respective common inlet and outlet adapted to communicate with a pipe through which the gas whose density is to be determined flows, whereby the gas circulates into each chamber by diffusion.

13. A sensor as claimed in claim 1, wherein each chamber has an inlet and an outlet, and the gas whose density is to be determined is arranged to flow through both chambers in parallel.

14. A sensor for use in determining the density of a gas, the sensor comprising:
a cavity arranged to receive the gas whose density is to be determined; and
a diaphragm dividing the cavity into two distinct chambers;
the sensor being characterised by:
excitation means for exciting the gas in the cavity into resonant vibration in a first mode in which the diaphragm vibrates with the gas, and in a second mode in which the diaphragm does not significantly take part in the vibration of the gas; and
pick-up means for sensing the respective frequencies of the first and second modes of vibration;
whereby the density of the gas may be determined from said frequencies.

15. A sensor as claimed in claim 14, wherein the position of the diaphragm within the cavity and the modes of vibration of the gas are selected such that the first mode has an antinode at the diaphragm, and the second mode has a node at the diaphragm.

16. A sensor as claimed in claim 15, wherein the diaphragm is positioned substantially midway between the opposite ends of the cavity, whereby the two chambers are of substantially equal length, and the first and second modes are modes 1 and 2 respectively.

17. A sensor as claimed in claim 14 wherein the excitation means and the pick-up means are piezoelectric.

18. A sensor as claimed in claim 14 wherein the or each cavity is substantially cylindrical, with its excitation means mounted in one end wall and its pick-up means mounted in the other end wall.

19. A sensor as claimed in claim 14 wherein each chamber has a respective common inlet and outlet adapted to communicate with a pipe through which the gas whose density is to be determined flows, whereby the gas circulates in to each chamber by diffusion.

20. A sensor as claimed in claim 14 wherein each chamber has an inlet and an outlet, and the gas whose density is to be determined is arranged to flow through both chambers in parallel.

21. A sensor for use in determining the density of a gas, the sensor comprising:
a first cavity arranged to receive a gas whose density is to be determined; and
a diaphragm dividing the first cavity into two distinct chambers;
the sensor being characterised by:
first excitation means for exciting the gas in the first cavity into resonant vibration in a mode in which the diaphragm vibrates with the gas;
first pick-up means for sensing the frequency of the vibration of the gas in the first cavity;
a second cavity arranged to receive the gas whose density is to be determined;
second excitation means for exciting the gas in the second cavity into resonant vibration; and
second pick-up means for sensing the frequency of the vibration of the gas in the second cavity;
whereby the density of the gas may be determined from said frequencies.

22. A sensor as claimed in claim 21, wherein the dimensions of the second cavity and/or the mode of vibration of the gas therein are selected such that the respective frequencies of vibration of the gas in the two cavities are similar.

23. A sensor as claimed in claim 21, wherein the position of the diaphragm within the first cavity and the mode of vibration of the gas in the first cavity are selected such that the mode has an antinode at the diaphragm.

24. A sensor as claimed in claim 23, wherein the diaphragm is positioned substantially midway between the opposite ends of the first cavity, whereby the two chambers are of substantially equal length, and the mode of vibration of the gas in the first cavity is the mode 1.

25. A sensor as claimed in claim 21 wherein the excitation means and the pick-up means are piezoelectric.

26. A sensor as claimed in claim 21 wherein the or each cavity is substantially cylindrical, with its excitation means mounted in one end wall and its pick-up means mounted in the other end wall.

27. A sensor as claimed in claim 21 wherein each chamber has a respective common inlet and outlet adapted to communicate with a pipe through which the gas whose density is to be determined flows, whereby the gas circulates into each chamber by diffusion.

28. A sensor as claimed in claim 21 wherein each chamber has an inlet and an outlet, and the gas whose density is to be determined is arranged to flow through both chambers in parallel.

* * * * *